(12) United States Patent
Watanabe et al.

(10) Patent No.: US 10,365,090 B2
(45) Date of Patent: Jul. 30, 2019

(54) IMAGING DEVICE AND IMAGING METHOD

(71) Applicant: FUJIFILM Corporation, Tokyo (JP)

(72) Inventors: Mikio Watanabe, Saitama (JP);
Fuminori Irie, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/845,233

(22) Filed: Dec. 18, 2017

(65) Prior Publication Data

US 2018/0106605 A1 Apr. 19, 2018

Related U.S. Application Data

(63) Continuation of application No. PCT/JP2016/066236, filed on Jun. 1, 2016.

(30) Foreign Application Priority Data

Jun. 29, 2015 (JP) .................................. 2015-130132

(51) Int. Cl.
*G01B 11/24* (2006.01)
*H04N 5/232* (2006.01)
(Continued)

(52) U.S. Cl.
CPC .............. *G01B 11/24* (2013.01); *G01B 11/26* (2013.01); *G01M 5/0008* (2013.01);
(Continued)

(58) Field of Classification Search
CPC ......... G01B 11/24; G01B 11/26; G06F 16/00; H04N 13/239; H04N 5/23293;
(Continued)

(56) References Cited

U.S. PATENT DOCUMENTS

2009/0125147 A1 5/2009 Wang et al.
2015/0148955 A1 5/2015 Chin et al.
(Continued)

FOREIGN PATENT DOCUMENTS

CN 1568489 A 1/2005
CN 101014110 A 8/2007
(Continued)

OTHER PUBLICATIONS

International Preliminary Report on Patentability and English translation (Form PCT/IPEA/409) for Application No. PCT/JP2016/066236, dated Feb. 16, 2017.
(Continued)

*Primary Examiner* — Mekonnen D Dagnew
(74) *Attorney, Agent, or Firm* — Birch, Stewart, Kolasch & Birch, LLP

(57) ABSTRACT

In an aspect of the invention, first and second images having parallax are acquired by an imaging unit (202) including a first imaging part (202A) and a second imaging part (202B), and an angle between an imaging direction of the imaging unit (202) and a normal direction of a flat surface of an object to be inspected having the flat surface is calculated on the basis of the acquired first and second images. The pan/tilt of the imaging unit (202) are controlled by a pan/tilt control unit (210), but images for inspection showing the object to be inspected are taken and acquired by the imaging unit in a case in which the calculated angle is controlled to an angle within an allowable angle range.

15 Claims, 10 Drawing Sheets

(51) Int. Cl.
*G06F 16/00* (2019.01)
*G01B 11/26* (2006.01)
*G01N 21/88* (2006.01)
*G01M 5/00* (2006.01)
*H04N 5/225* (2006.01)
*H04N 13/239* (2018.01)
*H04N 13/00* (2018.01)

(52) U.S. Cl.
CPC .......... *G01M 5/0091* (2013.01); *G01N 21/88* (2013.01); *G06F 16/00* (2019.01); *H04N 5/2252* (2013.01); *H04N 5/23203* (2013.01); *H04N 5/23229* (2013.01); *H04N 5/23293* (2013.01); *H04N 5/23299* (2018.08); *H04N 13/239* (2018.05); *H04N 2013/0081* (2013.01)

(58) Field of Classification Search
CPC ............. H04N 5/23229; H04N 5/2252; H04N 5/23299; H04N 5/23203; H04N 2013/0081; G01M 5/0091; G01M 5/0008; G01N 21/88
See application file for complete search history.

(56) References Cited

U.S. PATENT DOCUMENTS

| | | | |
|---|---|---|---|
| 2015/0237308 A1* | 8/2015 | Tanaka | H04N 7/18 348/86 |
| 2016/0055392 A1* | 2/2016 | Nakano | G06K 9/4633 382/173 |
| 2018/0074500 A1* | 3/2018 | Nonaka | G05B 19/00 |

FOREIGN PATENT DOCUMENTS

| | | | |
|---|---|---|---|
| CN | 104267043 | A | 1/2015 |
| JP | 62-105002 | A | 5/1987 |
| JP | 7-139909 | A | 6/1995 |
| JP | 2000-99740 | A | 4/2000 |
| JP | 2001-280960 | A | 10/2001 |
| JP | 2009-85785 | A | 4/2009 |
| JP | 2012-18073 | A | 1/2012 |

OTHER PUBLICATIONS

International Search Report and Written Opinion of the International Searching Authority (Forms PCT/ISA/210 and PCT/ISA/237) for Application No. PCT/JP2016/066236, dated Aug. 23, 2016, with an English translation of the Search Report.

Japanese Decision to Grant a Patent and English translation for Application No. 2017-526228, dated Jan. 5, 2018.

Ohya et al., "Development of inspection robot for under floor of house," Proceedings of the 2009 IEEE International Conference on Robotics and Automation, IEEE, May 12-17, 2009, pp. 1429-1434 (7 pages total).

Togawa et al., "Digital Gazo ni yoru Satsuei Kakudo to Ninshiki Kano na Hibiware Haba no Kensho," Proceedings of the Annual Conference of the Japan Society of Civil Engineers Part 1 (A), vol. 55, 2000, pp. 618 to 619.

Office Action and Search Report dated Apr. 26, 2019 in corresponding Chinese Patent Application No. 201680037808.4, along with English translation.

* cited by examiner

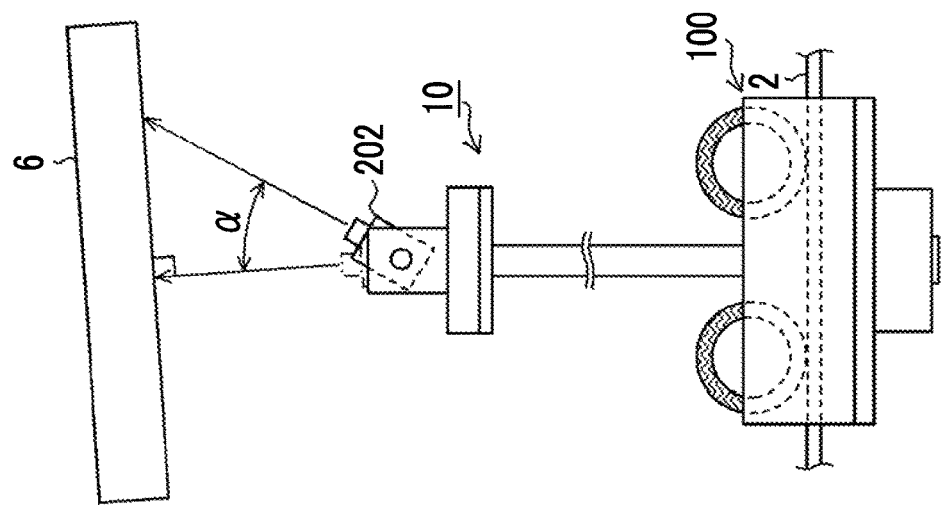
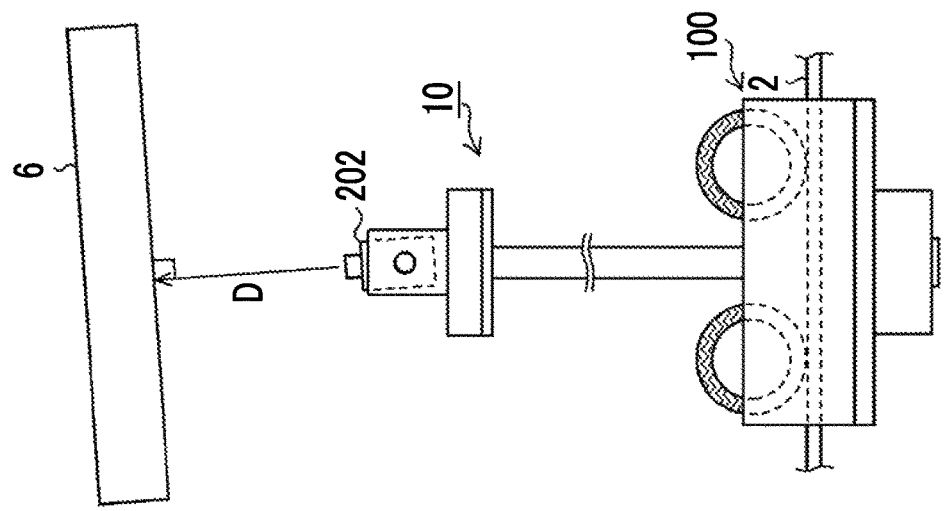
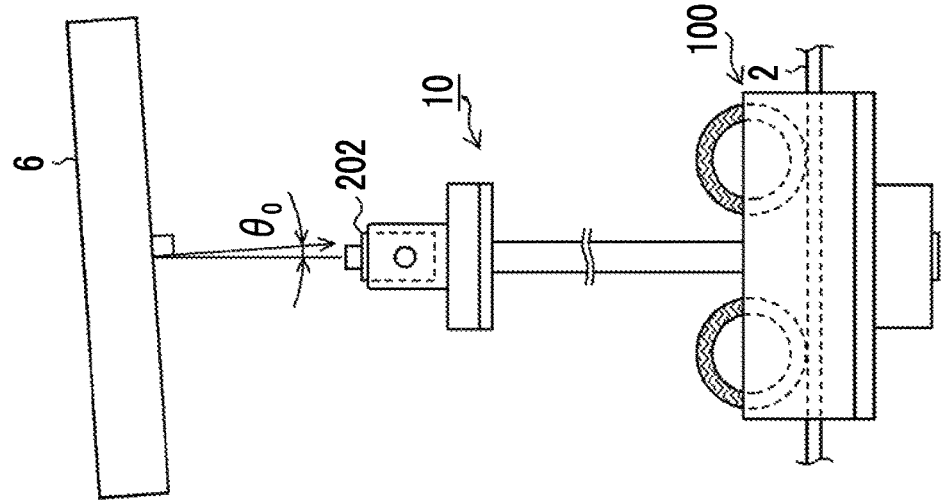

IMAGING DEVICE AND IMAGING METHOD

CROSS-REFERENCE TO RELATED APPLICATIONS

The present application is a Continuation of PCT International Application No. PCT/JP2016/066236 filed on Jun. 1, 2016 claiming priority under 35 U.S.C § 119(a) to Japanese Patent Application No. 2015-130132 filed on Jun. 29, 2015. Each of the above applications is hereby expressly incorporated by reference, in their entirety, into the present application.

BACKGROUND OF THE INVENTION

1. Field of the Invention

The present invention relates to an imaging device and an imaging method, and more particularly, to an imaging device and an imaging method that perform the inspection, sensing, and the like of an object to be inspected, such as a bridge.

2. Description of the Related Art

A crack width measurement system, which takes the image of a wall surface (an object to be inspected) including a flat surface and measures the width of a crack generated on the wall surface from the taken image, has been proposed in the past (JP2009-85785A).

The crack width measurement system disclosed in JP2009-85785A includes an underfloor inspection robot (moving body) that includes a camera and a robot operating device that remotely operates the underfloor inspection robot, the underfloor inspection robot can travel on the surface of an underfloor in accordance with a command output from the robot operating device, and the camera is adapted to be rotatable with respect to the underfloor inspection robot in a pan direction and a tilt direction.

Further, in JP2009-85785A, in a case in which the camera captures the crack generated on the wall surface, the movement of a vehicle body of the underfloor inspection robot is controlled so that an angle between the optical axis of the camera and the wall surface is in an allowable angle range. In this case, an angle between the wall surface and a vehicle-body direction of the underfloor inspection robot is calculated on the basis of a distance to the wall surface that is measured by a pair of left and right distance sensors provided on the vehicle body, and a pan angle between the wall surface and the optical axis of the camera is calculated on the basis of the calculated angle and a pan angle of the camera with respect to the vehicle body (see FIG. 22 of JP2009-85785A).

Furthermore, a technique for combining a crack-scale image with the taken image to be capable of measuring the width of the crack from the taken image is disclosed in the crack width measurement system disclosed in JP2009-85785A.

SUMMARY OF THE INVENTION

As described above, the underfloor inspection robot disclosed in JP2009-85785A calculates the pan angle between the wall surface and the optical axis of the camera on the basis of the angle between the vehicle-body direction of the underfloor inspection robot and the wall surface and the pan angle of the camera with respect to the vehicle body, and calculates the angle between the optical axis of the camera and the wall surface on the basis of the calculated pan angle and the tilt angle of the camera with respect to the vehicle body. However, the calculation of the angle between the optical axis of the camera and the wall surface is performed on the premise that the floor surface on which the underfloor inspection robot travels is orthogonal to the wall surface. That is, in a case in which the floor surface (travel surface) on which the underfloor inspection robot travels is not orthogonal to the wall surface (the object to be inspected), the angle between the object to be inspected and the optical axis of the camera cannot be calculated.

Further, the movement of the underfloor inspection robot is controlled so that the angle between the optical axis of the camera and the object to be inspected is in the allowable angle range. However, JP2009-85785A discloses that it is not possible to deal with an error in the tilt direction (an error of the angle between the optical axis of the camera and the object to be inspected), even though the underfloor inspection robot is moved, but there is no big problem since the crack of the wall surface is generally generated in a vertical direction.

Furthermore, in the invention disclosed in JP2009-85785A, in order to calculate the pan angle between the optical axis of the camera and the object to be inspected, it is necessary to calculate the angle between the wall surface and the vehicle-body direction of the underfloor inspection robot on the basis of the distance to the wall surface that is measured by the pair of left and right distance sensors provided on the vehicle body. Accordingly, the pair of left and right distance sensors is required.

The invention has been made in consideration of the circumstances, and an object of the invention is to provide an imaging device and an imaging method that can calculate an angle between an imaging direction of the imaging device and a normal direction of a flat surface of an object to be inspected, even though the positioning of the imaging device is unknown, and can thus appropriately control the imaging direction of the imaging device with respect to the object to be inspected.

To achieve the object, an aspect of the invention provides an imaging device that images an object to be inspected including a flat surface. The imaging device comprises an imaging unit that includes a plurality of imaging parts taking a plurality of images having parallax, a pan/tilt mechanism that rotates the imaging unit in each of a pan direction and a tilt direction, an angle calculation unit that calculates an angle between an imaging direction of the imaging unit and a normal direction of the flat surface of the object to be inspected on the basis of the plurality of images taken by the imaging unit and showing the object to be inspected, a pan/tilt control unit that controls the pan/tilt mechanism and sets the angle between the imaging direction of the imaging unit and the normal direction of the flat surface of the object to be inspected to an angle within an allowable angle range, and an imaging control unit that makes at least one imaging part of the imaging unit take images for inspection showing the object to be inspected to acquire the images for inspection in a case in which the angle between the imaging direction of the imaging unit and the normal direction of the flat surface of the object to be inspected is an angle within the allowable angle range.

According to the aspect of the invention, the angle between the imaging direction of the imaging unit and the normal direction of the flat surface of the object to be inspected is calculated on the basis of the plurality of images that are taken by the imaging unit and show the object to be inspected. Accordingly, a special distance sensor is not required, and the angle between the imaging direction of the imaging unit and the normal direction of the flat surface of the object to be inspected can be calculated even though the positioning of the imaging unit is unknown. Further, the imaging direction of the imaging unit with respect to the object to be inspected can be appropriately controlled by the angle calculated as described above (that is, the pan/tilt mechanism can be controlled so that the calculated angle is an angle within the allowable angle range), so that the images for inspection having required definition can be taken.

According to another aspect of the invention, in the imaging device, the angle calculation unit includes a corresponding point detection unit that detects three or more corresponding points, which are not positioned on the same straight line, from the plurality of images and a spatial coordinate calculation unit that calculates spatial coordinates of the three or more corresponding points detected by the corresponding point detection unit; and the angle calculation unit estimates the flat surface of the object to be inspected from the calculated spatial coordinates of the three or more corresponding points, and calculates the angle between the imaging direction of the imaging unit and the normal direction of the flat surface of the object to be inspected on the basis of the normal direction of the estimated flat surface.

According to another aspect of the invention, three or more corresponding points, which are not positioned on the same straight line, are detected from the plurality of images and the spatial coordinates of the detected three or more corresponding points are calculated. Here, the spatial coordinates are coordinate values on the coordinate system based on the imaging unit at the time of imaging, and the spatial coordinates of three or more points positioned on the flat surface of the object to be inspected are calculated on the coordinate system based on the imaging unit. The flat surface of the object to be inspected can be estimated from the spatial coordinates of three or more points, and the normal direction of the estimated flat surface (that is, the angle between the imaging direction of the imaging unit and the normal direction of the flat surface of the object to be inspected) can be calculated.

According to another aspect of the invention, in the imaging device, it is preferable that the allowable angle range is an angle range in which definition of the images for inspection at an end portion of an angle of view most distant from the imaging unit is the minimum definition required for the inspection accuracy of the object to be inspected, in a case in which the angle between the imaging direction of the imaging unit and the normal direction of the flat surface of the object to be inspected is the maximum angle within the allowable angle range. Accordingly, the taken images for inspection have the minimum definition required for the inspection accuracy of the object to be inspected.

According to another aspect of the invention, in the imaging device, it is preferable that the imaging unit includes an imaging optical system of which an imaging magnification is adjustable and the allowable angle range is set in accordance with the imaging magnification of the imaging optical system. The reason for this is that spatial resolution becomes high as the imaging magnification of the imaging optical system becomes high.

According to another aspect of the invention, it is preferable that the imaging device further comprises a live-view image display unit displaying a live-view image taken by at least one imaging part of the imaging unit, a pan/tilt operating unit outputting pan/tilt commands to the pan/tilt mechanism by a manual operation, and a determination unit determining whether or not the angle calculated by the angle calculation unit exceeds the allowable angle range, and the pan/tilt control unit controls the pan/tilt mechanism on the basis of the pan/tilt commands output from the pan/tilt operating unit and stops the pan/tilt mechanism in a case in which the determination unit determines that the angle calculated by the angle calculation unit exceeds the allowable angle range.

According to another aspect of the invention, an operator manually operates the pan/tilt mechanism while viewing the live-view image, and the pan/tilt mechanism is adapted to be stopped if it is determined that the angle between the imaging direction of the imaging unit and the normal direction of the flat surface of the object to be inspected exceeds the allowable angle range in a case in which a desired imaging range of the object to be inspected is to be imaged. Accordingly, the pan/tilt mechanism can be adapted not to be manually operated beyond the allowable angle range.

According to another aspect of the invention, it is preferable that the imaging device further comprises a live-view image display unit displaying a live-view image taken by at least one imaging part of the imaging unit, a pan/tilt operating unit outputting pan/tilt commands to the pan/tilt mechanism by a manual operation, a determination unit determining whether or not the angle calculated by the angle calculation unit exceeds the allowable angle range, and an information unit issuing a warning in a case in which the determination unit determines that the angle calculated by the angle calculation unit exceeds the allowable angle range, and the pan/tilt control unit controls the pan/tilt mechanism on the basis of the pan/tilt commands output from the pan/tilt operating unit.

According to another aspect of the invention, an operator manually operates the pan/tilt mechanism while viewing the live-view image, and a warning is adapted to be issued if it is determined that the angle between the imaging direction of the imaging unit and the normal direction of the flat surface of the object to be inspected exceeds the allowable angle range in a case in which a desired imaging range of the object to be inspected is to be imaged. Accordingly, the pan/tilt mechanism can be adapted not to be manually operated beyond the allowable angle range.

According to another aspect of the invention, in the imaging device, it is preferable that the pan/tilt control unit automatically controls the pan/tilt mechanism on the basis of the angle calculated by the angle calculation unit to set the angle between the imaging direction of the imaging unit and the normal direction of the flat surface of the object to be inspected to 0°. Accordingly, the imaging unit can be automatically made to directly face the object to be inspected in a case in which the object to be inspected is to be imaged by the imaging unit.

According to another aspect of the invention, it is preferable that the imaging device further comprises a moving body on which the imaging device is mounted and which moves the imaging device along the flat surface of the object to be inspected, a moving body operating unit outputting a movement command to the moving body by a manual operation, and a moving body control unit moving the moving body on the basis of the movement command output from the moving body operating unit.

According to another aspect of the invention, the moving body on which the imaging device is mounted can be moved along the flat surface of the object to be inspected. Accordingly, even though the angle between the imaging direction of the imaging unit and the normal direction of the flat surface of the object to be inspected cannot be made to be in the allowable angle range through the control of the pan/tilt mechanism in a case in which a desired imaging range of the object to be inspected is to be imaged, the angle can be made to be in the allowable angle range by the movement of the moving body.

According to another aspect of the invention, it is preferable that the imaging device further comprises an image recording unit recording the images for inspection acquired by the imaging control unit in association with the angle between the imaging direction of the imaging unit and the normal direction of the flat surface of the object to be inspected at the time of taking the images for inspection.

According to another aspect of the invention, it is preferable that the imaging device further comprises a distance calculation unit calculating a distance between the object to be inspected and the imaging unit in the imaging direction of the imaging unit on the basis of the plurality of images taken by the imaging unit and showing the object to be inspected and an image recording unit recording the images for inspection acquired by the imaging control unit in association with the angle between the imaging direction of the imaging unit and the normal direction of the flat surface of the object to be inspected at the time of taking the images for inspection and the distance calculated by the distance calculation unit. Since the angle between the imaging direction of the imaging unit and the normal direction of the flat surface of the object to be inspected and the distance are recorded in association with the images for inspection, the actual size of a portion of interest (for example, a crack or the like) of the object to be inspected can be grasped from the images for inspection.

According to another aspect of the invention, in the imaging device, it is preferable that the imaging unit includes an imaging optical system of which an imaging magnification is adjustable and the image recording unit records the images for inspection in association with the angle between the imaging direction of the imaging unit and the normal direction of the flat surface of the object to be inspected at the time of taking the images for inspection, the distance calculated by the distance calculation unit, and the imaging magnification of the imaging optical system. Since the angle between the imaging direction of the imaging unit and the normal direction of the flat surface of the object to be inspected, the distance, and the imaging magnification of the imaging optical system are recorded in association with the images for inspection, the actual size of a portion of interest of the object to be inspected can be grasped from the images for inspection.

According to another aspect of the invention, in the imaging device, it is preferable that the angle calculation unit calculates the angle between the imaging direction of the imaging unit and the normal direction of the flat surface of the object to be inspected on the basis of the plurality of images taken and acquired by the imaging unit at the time of taking the images for inspection and showing the object to be inspected. According to this, an angle detector for detecting the pan angle and the tilt angle of the pan/tilt mechanism can be omitted and the angle between the imaging direction of the imaging unit and the normal direction of the flat surface of the object to be inspected at the time of taking the images for inspection can be accurately detected without depending on the detection accuracy of the angle detector.

Another aspect of the invention provides an imaging method of imaging an object to be inspected including a flat surface. The imaging method comprises: a step of taking a plurality of images having parallax by an imaging unit including a plurality of imaging parts; a step of calculating an angle between an imaging direction of the imaging unit and a normal direction of the flat surface of the object to be inspected on the basis of the plurality of images, which are taken by the imaging unit and show the object to be inspected, by an angle calculation unit; a step of controlling a pan/tilt mechanism, which rotates the imaging unit in each of a pan direction and a tilt direction, and setting the angle between the imaging direction of the imaging unit and the normal direction of the flat surface of the object to be inspected to an angle within an allowable angle range; and a step of making at least one imaging part of the imaging unit take images for inspection showing the object to be inspected to acquire the images for inspection in a case in which the angle between the imaging direction of the imaging unit and the normal direction of the flat surface of the object to be inspected is an angle within the allowable angle range.

According to another aspect of the invention, in the imaging method, the step of calculating the angle includes a step of detecting three or more corresponding points, which are not positioned on the same straight line, from the plurality of images and a step of calculating spatial coordinates of the detected three or more corresponding points, and the flat surface of the object to be inspected is estimated from the calculated spatial coordinates of the three or more corresponding points and the angle between the imaging direction of the imaging unit and the normal direction of the flat surface of the object to be inspected is calculated on the basis of the normal direction of the estimated flat surface.

According to another aspect of the invention, in the imaging method, it is preferable that the allowable angle range is an angle range in which definition of the images for inspection at an end portion of an angle of view most distant from the imaging unit is the minimum definition required for the inspection accuracy of the object to be inspected, in a case in which the angle between the imaging direction of the imaging unit and the normal direction of the flat surface of the object to be inspected is the maximum angle within the allowable angle range.

According to the invention, the angle between the imaging direction of the imaging unit and the normal direction of the flat surface of the object to be inspected is calculated on the basis of the plurality of images that are taken by the imaging unit and show the object to be inspected. Accordingly, even though the positioning of the imaging unit is unknown, the angle between the imaging direction of the imaging unit and the normal direction of the flat surface of the object to be inspected can be calculated. Therefore, the imaging direction of the imaging unit with respect to the object to be inspected can be appropriately controlled.

BRIEF DESCRIPTION OF THE DRAWINGS

FIGS. 9A, 9B, and 9C are schematic diagrams schematically showing the imaging method of the first embodiment.

DESCRIPTION OF THE PREFERRED EMBODIMENTS

Embodiments of an imaging device and a method of controlling the movement of the imaging device according to the invention will be described below with reference to accompanying drawings.

[Structure of Bridge]

Figure 1:
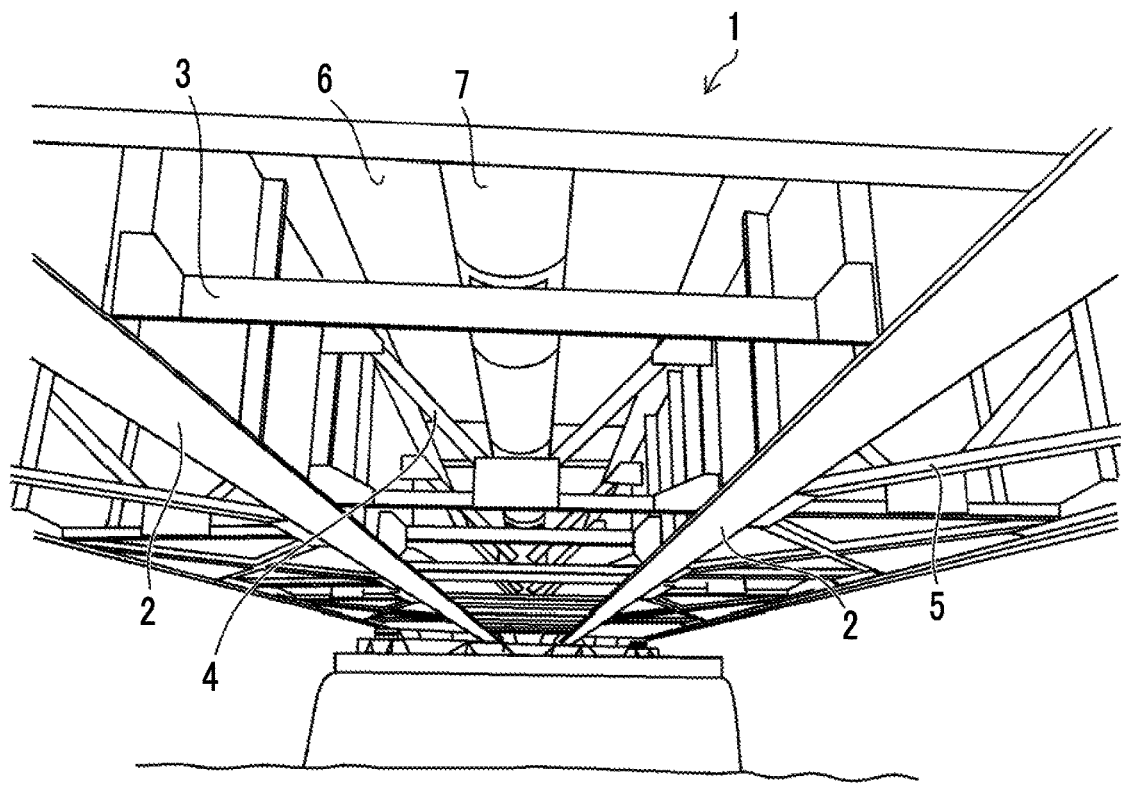
FIG. 1 is a diagram showing the appearance of a bridge seen from the lower surface side.

FIG. 1 is a perspective view showing the structure of a bridge that is one of the objects to be inspected which are to be imaged by an imaging device according to the invention, and is a perspective view of the bridge seen from below.

The bridge 1 shown in FIG. 1 includes main girders 2, cross beams 3, cross frames 4, and lateral frames 5; and the main girders 2, the cross beams 3, the cross frames 4, and the lateral frames 5 are connected to each other by bolts, rivets, or welding. Further, floor slabs 6 on which vehicles and the like travel are installed on the main girders 2 and the like. The floor slabs 6 are generally made of reinforced concrete.

The main girder 2 is a member that is provided between abutments or piers and supports the load of vehicles and the like present on the floor slab 6. The cross beam 3 is a member that connects the main girders 2 to support a load by the plurality of main girders 2. The cross frame 4 and the lateral frame 5 are members that connect the main girders 2 to resist a lateral load of wind, earthquake, or the like. Further, pipes 7 are provided below the bridge 1 of this example.

In the case of the bridge 1, an object to be inspected having a flat surface is the floor slab 6 and the back surface of the floor slab 6 is imaged in an embodiment to be described below.

[Appearance of Imaging Device]

Figure 2:
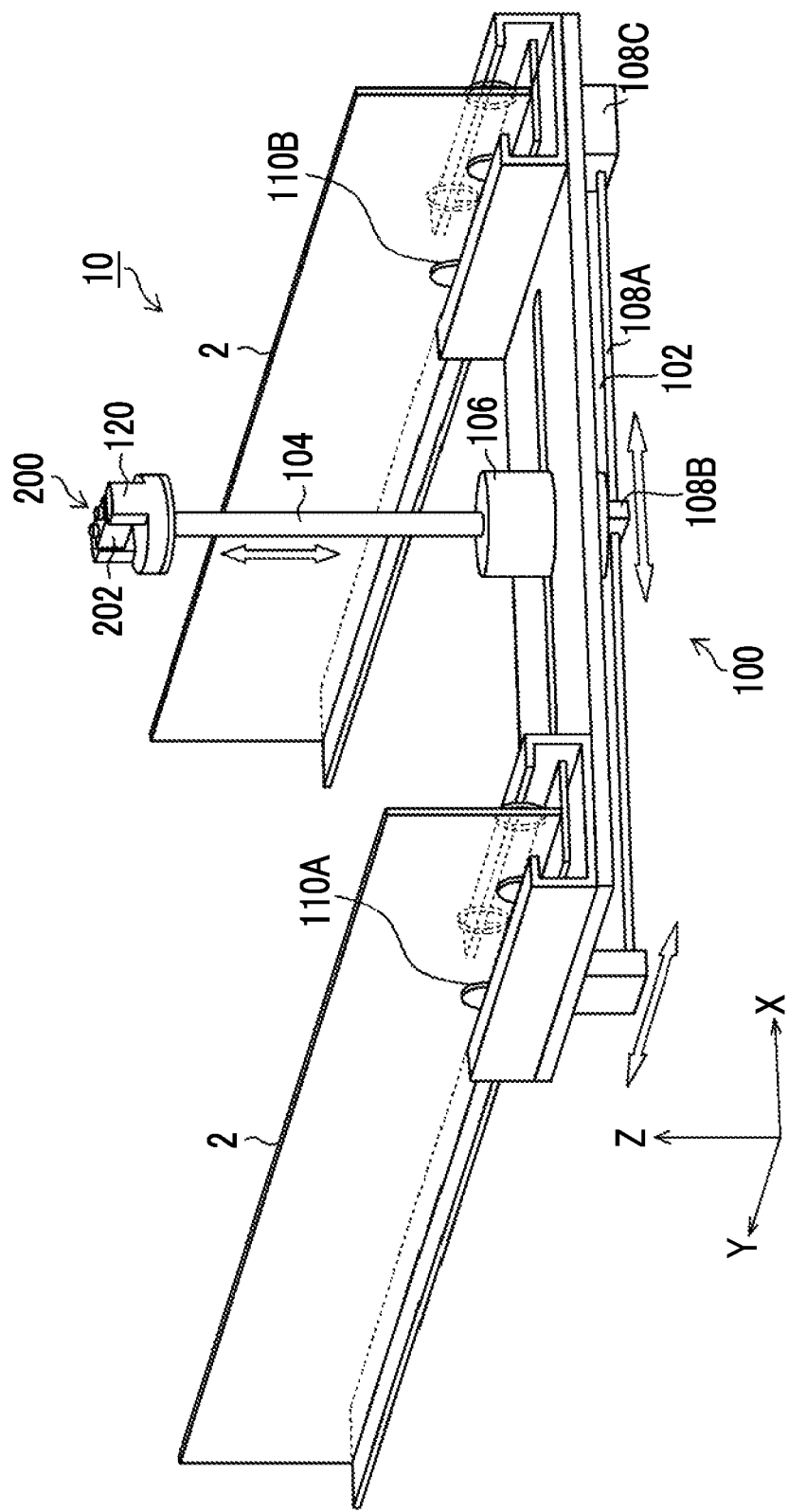
FIG. 2 is a perspective view showing the appearance of a movable imaging apparatus that includes an imaging device according to the invention.

FIG. 2 is a perspective view showing the appearance of a movable imaging apparatus that includes an imaging device according to the invention, and shows a state in which the movable imaging apparatus is installed between the main girders 2 of the bridge 1. Further, FIG. 3 is a cross-sectional view of main parts of the movable imaging apparatus shown in FIG. 2.

Figure 3:
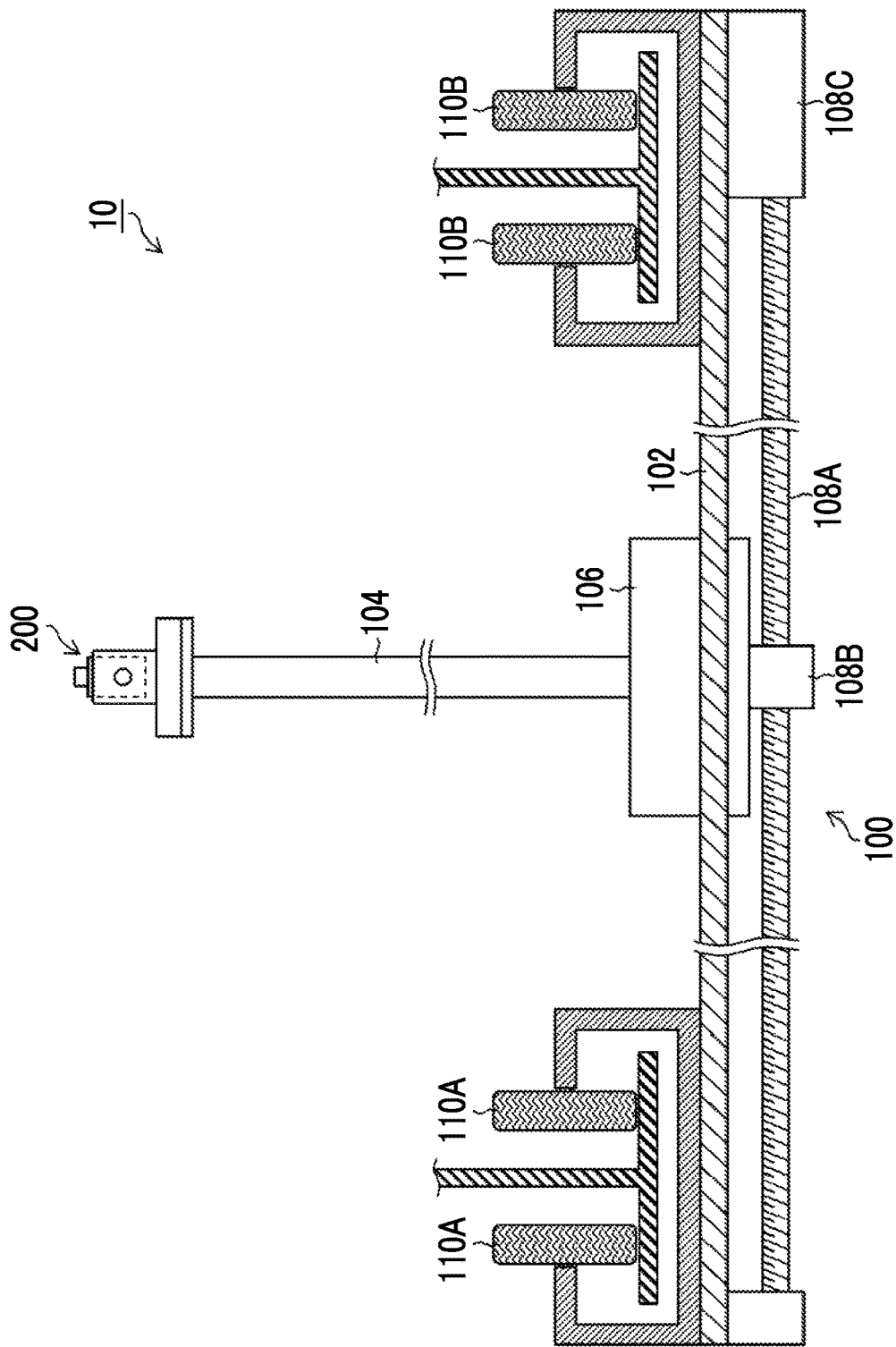
FIG. 3 is a cross-sectional view of main parts of the movable imaging apparatus shown in FIG. 2.

As shown in FIGS. 2 and 3, the movable imaging apparatus 10 mainly includes a robot device 100 that functions as a moving body and an imaging device 200 that is mounted on the robot device 100.

Although described in detail later, the robot device 100 includes a main frame 102, a vertical telescopic arm 104, a housing 106 in which various drive units, various control units, and the like for the vertical telescopic arm 104 are provided, an X-direction drive unit 108 (FIG. 5) that moves the housing 106 in a longitudinal direction of the main frame 102 (a direction orthogonal to the longitudinal direction of the main girder 2) (X direction), a Y-direction drive unit 110 (FIG. 5) that moves the entire movable imaging apparatus 10 in the longitudinal direction of the main girder 2 (Y direction), and a Z-direction drive unit 112 (FIG. 5) that makes the vertical telescopic arm 104 elongate and contract in a vertical direction (Z direction).

The X-direction drive unit 108 includes a ball screw 108A that is provided in the longitudinal direction of the main frame 102 (X direction), a ball nut 108B that is provided in the housing 106, and a motor 108C that rotates the ball screw 108A; and rotates the ball screw 108A in a normal direction or a reverse direction by the motor 108C to move the housing 106 in the X direction.

The Y-direction drive unit 110 includes tires 110A and 110B that are provided at both ends of the main frame 102 and motors (not shown) that are provided in the tires 110A and 110B; and drives the tires 110A and 110B by the motors to move the entire movable imaging apparatus 10 in the Y direction.

The movable imaging apparatus 10 is installed in an aspect in which the tires 110A and 110B provided at both ends of the main frame 102 are placed on lower flanges of the two main girders 2 and are disposed so that each of the two main girders 2 is positioned between the tires 110A and 110B. Accordingly, the movable imaging apparatus 10 can move (be self-propelled) along the main girders 2 while being suspended from the lower flanges of the main girders 2. Further, although not shown, the main frame 102 is adapted so that the length of the main frame 102 can be adjusted in accordance with an interval between the main girders 2.

The vertical telescopic arm 104 is provided in the housing 106 of the robot device 100, and is moved in the X direction and the Y direction together with the housing 106. Further, the vertical telescopic arm 104 is made to elongate and contract in the Z direction by the Z-direction drive unit 112 (FIG. 5) that is provided in the housing 106.

Figure 4:
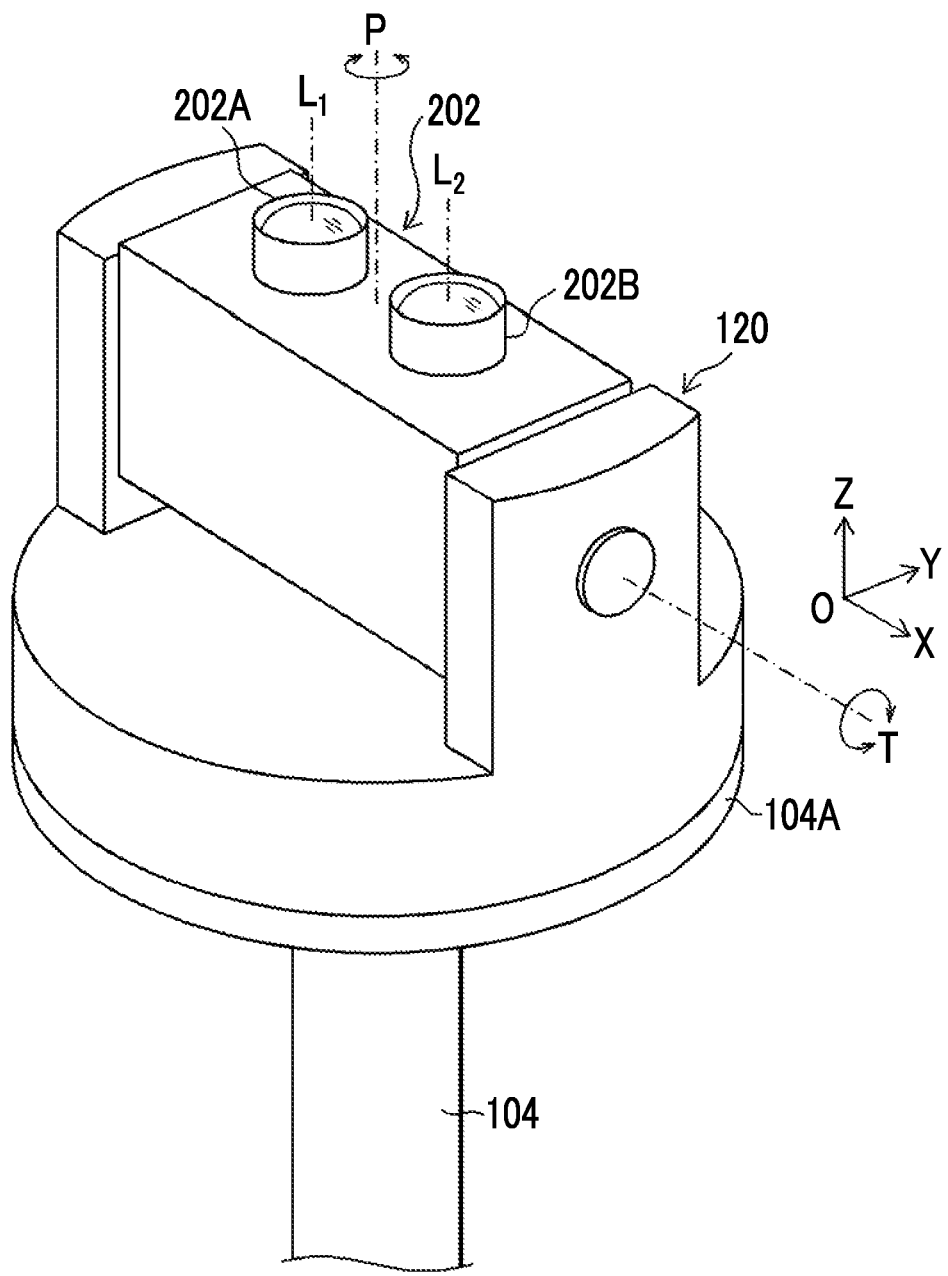
FIG. 4 is a perspective view showing the appearance of an imaging unit and a pan/tilt mechanism.

A camera installation part 104A is provided at the end of the vertical telescopic arm 104 as shown in FIG. 4, and an imaging unit 202, which can be rotated in a pan direction and a tilt direction by a pan/tilt mechanism 120, is installed on the camera installation part 104A.

The imaging unit 202 includes a first imaging part 202A and a second imaging part 202B, and can take two images (stereoscopic images) having parallax by the first and second imaging parts 202A and 202B. The stereoscopic image may be any one of a video and a static image.

Figure 5:
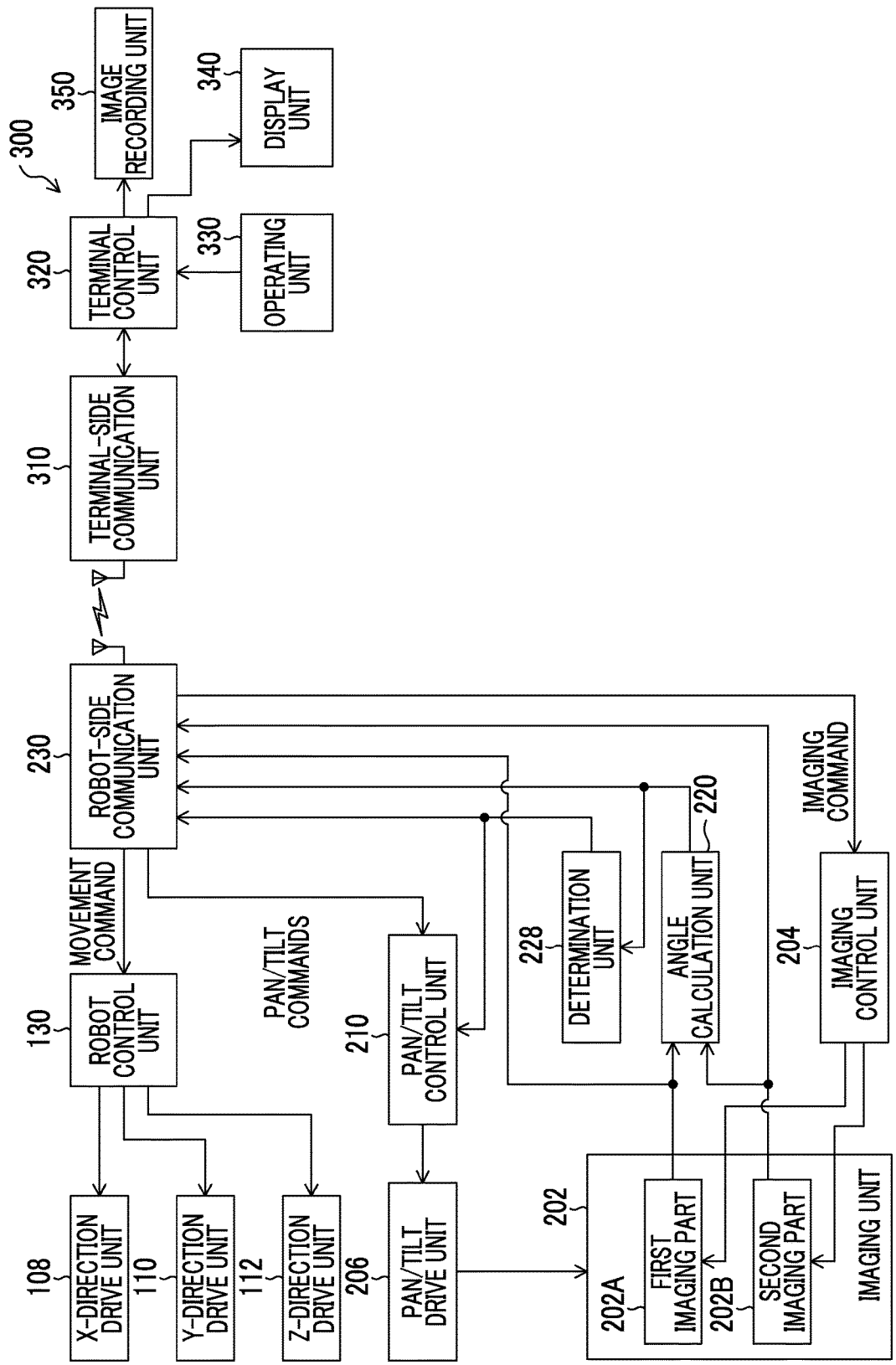
FIG. 5 is a block diagram of an embodiment of the movable imaging apparatus that includes the imaging device according to the invention.

The imaging unit 202 is rotated about a pan axis P coaxial with the vertical telescopic arm 104 or is rotated about a tilt axis T parallel to a horizontal direction by the pan/tilt mechanism 120 to which a driving force is applied from a pan/tilt drive unit 206 (FIG. 5). Accordingly, the imaging unit 202 can take images in an arbitrary positioning (take images in an arbitrary imaging direction).

Each of an optical axis $L_1$ of the first imaging part 202A of the imaging unit 202 of this example and an optical axis $L_2$ of the second imaging part 202B is parallel to the pan axis P, and the pan axis P is positioned in the middle between the optical axis $L_1$ and the optical axis $L_2$. Further, the pan axis P is orthogonal to the tilt axis T. Furthermore, the base length of the imaging unit 202 (that is, an installation interval between the first imaging part 202A and the second imaging part 202B) is already known.

Further, a coordinate system, which is based on the imaging unit 202, uses an intersection point between the pan axis P and the tilt axis T as an origin O; and the direction of the tilt axis T is referred to as an x-axis direction, the direction of the pan axis P is referred to as a z-axis direction, and a direction orthogonal to an x axis and a y axis is referred to as a y-axis direction.

<Configuration of Movable Imaging Apparatus 10>

FIG. 5 is a block diagram of an embodiment of the movable imaging apparatus that includes the imaging device according to the invention.

As shown in FIG. 5, the movable imaging apparatus 10 includes: a robot control unit (moving body control unit) 130, the X-direction drive unit 108, the Y-direction drive unit 110, and the Z-direction drive unit 112 of the robot device (moving body) 100; the imaging unit 202, an imaging control unit 204, a pan/tilt control unit 210, a pan/tilt drive unit 206, an angle calculation unit 220, and a determination unit 228 of the imaging device 200; a robot-side communication unit 230; and a terminal device 300.

The robot-side communication unit 230 performs two-way radio communication between a terminal-side communication unit 310 and itself; receives various commands, such as a movement command for controlling the movement of the robot device 100, a pan/tilt command for controlling the pan/tilt mechanism 120, and an imaging command for controlling the imaging unit 202, which are transmitted from the terminal-side communication unit 310; and outputs the received commands to the corresponding control units, respectively. The detail of the terminal device 300 will be described later.

The robot control unit 130 controls the X-direction drive unit 108, the Y-direction drive unit 110, and the Z-direction drive unit 112 on the basis of a movement command, which is input from the robot-side communication unit 230, to make the robot device 100 move in the X direction and the Y direction and to make the vertical telescopic arm 104 elongate and contract in the Z direction (see FIG. 2).

The pan/tilt control unit 210 makes the pan/tilt mechanism 120 be operated in the pan direction and the tilt direction by the pan/tilt drive unit 206 on the basis of a pan/tilt command, which is input from the robot-side communication unit 230, to pan and tilt the imaging unit 202 in a desired direction (see FIG. 4).

Further, since a determination result obtained from the determination unit 228 is added to other inputs of the pan/tilt control unit 210, the pan/tilt control unit 210 becomes operable or inoperable in accordance with the determination result obtained from the determination unit 228. The detail of the determination unit 228 will be described later.

The imaging control unit 204 makes the first and second imaging parts 202A and 202B of the imaging unit 202 take a live-view image, images for angle calculation or images for inspection on the basis of an imaging command that is input from the robot-side communication unit 230. The images for angle calculation are two images (a first image and a second image) having parallax that are taken by the first and second imaging parts 202A and 202B, and it is preferable that the images for angle calculation are videos. In a case in which the images for angle calculation are videos, the live-view image may be the same images as the images for angle calculation or may be any one (for example, the first image) of the first and second images. Further, the images for inspection are two images (the first and second images) having parallax that are taken by the first and second imaging parts 202A and 202B, and it is preferable that the images for inspection are the largest images capable of being taken by the first and second imaging parts 202A and 202B.

Image data representing the first and second images having parallax, which are taken by the first and second imaging parts 202A and 202B of the imaging unit 202, are output to the angle calculation unit 220 and the robot-side communication unit 230, respectively.

The angle calculation unit 220 calculates an angle θ between the imaging direction of the imaging unit 202 (the same direction as the directions of the optical axes $L_1$ and $L_2$ of the first and second imaging parts 202A and 202B shown in FIG. 4 in the case of this example) and the normal direction of the flat surface of an object to be inspected (the floor slab 6 of the bridge 1 shown in FIG. 1 in the case of this example) on the basis of the image data representing the first and second images that are taken by the first and second imaging parts 202A and 202B.

<Method of Calculating Angle θ>

First, a meaning of the calculation of the angle θ between the imaging direction of the imaging unit 202 and the normal direction of the flat surface of an object to be inspected will be described.

Figure 6:
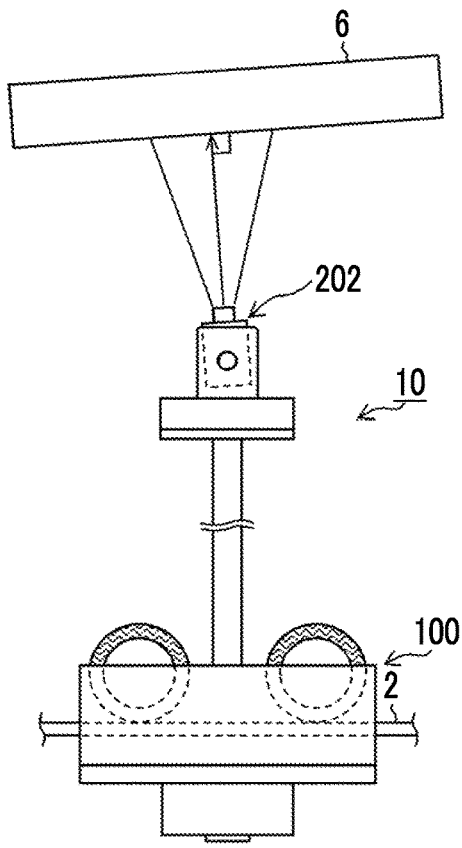
FIG. 6 is a diagram showing an aspect in which the back surface of an object to be inspected is imaged by the movable imaging apparatus.

FIG. 6 is a diagram showing an aspect in which the back surface of the object to be inspected (the floor slab 6) is imaged by the movable imaging apparatus 10.

The movable imaging apparatus 10 travels (moves) while being suspended from the lower flanges of the main girders 2, but the travel surface for the movable imaging apparatus 10 (the lower flanges of the main girders 2) and the back surface of the floor slab 6 are not necessarily parallel to each other. Accordingly, for example, even in a case in which the tilt angle of the imaging unit 202 is set to 0° and the optical axis of the imaging unit 202 is set to be parallel to a direction orthogonal to the travel surface, the imaging unit 202 cannot be made to directly face the back surface of the floor slab 6 (that is, the angle θ between the optical axis direction of the imaging unit 202 and the normal direction of the flat surface of the object to be inspected cannot be set to 0°).

In a case in which the angle θ is 0°, images for inspection having the highest definition can be taken. As the angle θ is increased, the definition of the images for inspection (particularly, the definition of the images for inspection at an end portion of an angle of view distant from the imaging unit 202) is lowered. Accordingly, there is a case where definition required for the inspection accuracy of the object to be inspected may not be obtained.

Accordingly, the angle θ needs to be detected to pan and tilt the imaging unit 202 so that the angle θ between the optical axis direction of the imaging unit 202 and the normal direction of the flat surface of the object to be inspected is set to 0° (so that the imaging unit 202 is made to face the object to be inspected) or to pan and tilt the imaging unit 202 so that the angle θ is in the minimum angle range in which definition required for the inspection accuracy of the object to be inspected is obtained (allowable angle range).

Accordingly, in the invention, the angle θ between the imaging direction of the imaging unit 202 and the normal direction of the flat surface of the object to be inspected is calculated by a method to be described below on the basis of the image data representing the first and second images that are taken by the first and second imaging parts 202A and 202B.

Figure 7:
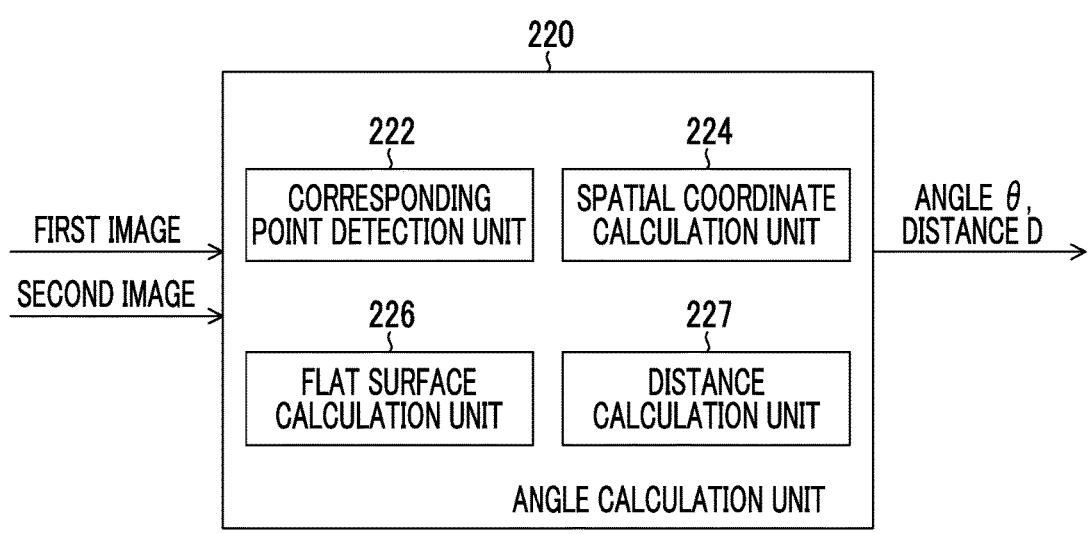
FIG. 7 is a functional block diagram showing the configuration of an angle calculation unit shown in FIG. 5.

FIG. 7 is a functional block diagram showing the configuration of the angle calculation unit 220 shown in FIG. 5. The angle calculation unit 220 includes a corresponding point detection unit 222, a spatial coordinate calculation unit 224, a flat surface calculation unit 226, and a distance calculation unit 227.

The corresponding point detection unit 222 detects three or more corresponding points, which are not positioned on the same straight line, on the basis of the first and second images having parallax that are taken by the first and second imaging parts 202A and 202B of the imaging unit 202. For example, the corresponding point detection unit 222 detects three characteristic points, which are not positioned on the same straight line, from the first image and detects corresponding points, which correspond to the detected three characteristic points, from the second image. In regard to the detection of the corresponding points from the second image, the corresponding point detection unit 222 scans the second image on the basis of the image of a local region of the first image including the characteristic points and can detect positions (points), between which correlation is highest on the second image, as the corresponding points. These three characteristic points and the three corresponding points corresponding to the three characteristic points are three pairs of corresponding points corresponding to each other.

The spatial coordinate calculation unit 224 calculates spatial coordinates (x, y, z) of the three corresponding points on a real space (the flat surface of the object to be inspected) in the coordinate system based on the imaging unit 202 described in FIG. 4. The spatial coordinate calculation unit 224 can geometrically calculate the spatial coordinates of the corresponding points on the basis of the positions of the corresponding points on the first image, the positions of the corresponding points on the second image, the base length between the first and second imaging parts 202A and 202B, and the imaging magnifications of imaging optical systems of the first and second imaging parts 202A and 202B.

The flat surface calculation unit 226 estimates the flat surface of the object to be inspected on the basis of the spatial coordinates of the three corresponding points calculated by the spatial coordinate calculation unit 224, and calculates the angle θ between the imaging direction of the imaging unit 202 and the normal direction of the flat surface of the object to be inspected on the basis of the normal direction of the estimated flat surface.

An equation of the flat surface represented in the following equation is obtained on the basis of the spatial coordinates of three points on the flat surface, so that the flat surface of the object to be inspected can be estimated (specified).

$$ax+by+cz+d=0 \qquad \text{[Equation 1]}$$

Since the flat surface of the object to be inspected is specified as described above, a normal vector n of the flat surface of the object to be inspected can be expressed by "n=(a, b, c)". Further, the angle θ between the imaging direction of the imaging unit 202 (the z direction of the coordinate system based on the imaging unit 202) and the normal direction of the flat surface of the object to be inspected can be calculated from the normal vector n (n=(a, b, c)) by the following equation.

$$\theta=\arccos(c/\sqrt{(a^2+b^2+c^2)}) \qquad \text{[Equation 2]}$$

Further, a distance D between the imaging unit 202 and the object to be inspected (an imaging distance of the imaging unit 202 in the optical axis direction (z direction)) can be calculated by the following equation.

$$D=-d/c \qquad \text{[Equation 3]}$$

The angle calculation unit 220 outputs information representing the angle θ that is calculated by [Equation 2], and the distance calculation unit 227 outputs information representing the distance D that is calculated by [Equation 3].

Returning to FIG. 5, the information representing the angle θ and the distance D, which are calculated by the angle calculation unit 220, is added to the determination unit 228 and the robot-side communication unit 230.

An allowable angle range (−α to α) is set in the determination unit 228, and the determination unit 228 determines whether or not the angle θ calculated by the angle calculation unit 220 is in the allowable angle range. Here, the allowable angle range is set as an angle range in which the definition of the images for inspection at an end portion of the angle of view most distant from the imaging unit 202 is the minimum definition required for the inspection accuracy of the object to be inspected, in a case in which the angle θ between the imaging direction of the imaging unit 202 and the normal direction of the flat surface of the object to be inspected is the maximum angle (±α) within the allowable angle range.

Further, since the definition of the images for inspection (for example, the actual size of the object to be inspected per pixel of the imaging elements of the first and second imaging parts 202A and 202B) is changed in accordance with the distance D or the angle of view, it is preferable that the allowable angle range is set in accordance with an imaging magnification of an imaging optical system in the case of the imaging unit 202 including the imaging optical system, of which the imaging magnification (angle of view) can be adjusted, and is set in accordance with the distance D in a case in which the distance D is changed.

The determination result determined by the determination unit 228 (the determination result representing whether or not the angle θ calculated by the angle calculation unit 220 exceeds the allowable angle range) is output to each of the pan/tilt control unit 210 and the robot-side communication unit 230.

The pan/tilt control unit 210 controls the pan/tilt mechanism 120 through the pan/tilt drive unit 206 on the basis of a pan/tilt command and pans and tilts the imaging unit 202, but becomes operable or inoperable in accordance with the determination result added from the determination unit 228. That is, in a case in which the determination result representing that the angle θ exceeds the allowable angle range is input to the pan/tilt control unit 210 from the determination unit 228, the pan/tilt control unit 210 stops the pan/tilt mechanism 120 regardless of the input of the pan/tilt command. Accordingly, the pan/tilt of the imaging unit 202 can be adapted not to be controlled in a case in which the angle θ exceeds the allowable angle range.

The terminal device 300 is operated by an operator that operates the movable imaging apparatus 10. The terminal device 300 mainly includes the terminal-side communication unit 310, a terminal control unit 320, an operating unit 330, a display unit 340 that functions as a live-view image display unit and an information unit for a warning, and an image recording unit 350. For example, a tablet terminal can be applied.

The terminal-side communication unit 310 performs two-way radio communication between the robot-side communication unit 230 and itself, receives various kinds of information that is input by the robot-side communication unit 230 (the image data representing the live-view image and the images for inspection that are taken by the first and second imaging parts 202A and 202B, the information representing the angle θ and the distance D that are calculated by the angle calculation unit 220, and the determination result that is determined by the determination unit 228), and transmits various commands corresponding to the operations, which are input to the operating unit 330 through the terminal control unit 320, to the robot-side communication unit 230.

The terminal control unit 320 outputs the image data, which are received through the terminal-side communication unit 310 and represent the live-view image, to the display unit 340 and makes the live-view image be displayed on the screen of the display unit 340. Further, in a case in which the determination result determined by the determination unit 228 (the determination result representing that the angle θ exceeds the allowable angle range) is input to the terminal control unit 320, the terminal control unit 320 issues a warning (a warning mark, a warning message, or the like) through the display unit 340. The terminal control unit 320 may be adapted to generate a warning sound through a speaker (not shown).

The operating unit 330 includes a robot operating unit (moving body operating unit), a pan/tilt operating unit, and an imaging operating unit. The robot operating unit outputs movement commands for moving the robot device 100 (the imaging unit 202) in the X direction, the Y direction, and the Z direction; the pan/tilt operating unit outputs pan/tilt commands for rotating the pan/tilt mechanism 120 (the imaging unit 202) in the pan direction and the tilt direction; and the imaging operating unit outputs an imaging command for instructing the imaging unit 202 to take images for inspection. The operator manually operates the operating unit 330 while viewing the live-view image displayed on the display unit 340; and the operating unit 330 outputs various commands, such as the movement commands for moving the imaging unit 202 in the X direction, the Y direction, and the Z direction, the pan/tilt commands, and the imaging command, to the terminal control unit 320 in accordance with an operation performed by the operator. The terminal control unit 320 transmits various commands, which are input from the operating unit 330, to the robot-side communication unit 230 through the terminal-side communication unit 310.

Further, in a case in which the angle θ exceeds the allowable angle range, a warning is displayed on the display unit 340. Accordingly, in a case in which an operator operates the pan/tilt operating unit of the operating unit 330 to pan and tilt the imaging unit 202, the operator can operate the operating unit 330 so that the warning is not displayed on the display unit 340. Furthermore, if the angle θ cannot be made to be in the allowable angle range through the control of the pan/tilt mechanism 120 in a case in which a desired imaging range of an object to be inspected is to be imaged, an operator can make the angle θ be in the allowable angle range by operating the robot operating unit of the operating unit 330 to move the imaging unit 202 along the flat surface of the object to be inspected.

Further, the terminal control unit 320 outputs image data, which represent the images for inspection (the first image and the second image) received through the terminal-side communication unit 310, to the image recording unit 350, and the image recording unit 350 records the image data that are input from the terminal control unit 320 and represent the images for inspection. In this case, since the first and second images having parallax are recorded as the images for inspection, the sizes of portions of interest (a crack, a defect, and the like) can be grasped in a case in which the images for inspection are used afterward to inspect the object to be inspected.

Furthermore, it is preferable that the terminal control unit 320 records the images for inspection received through the terminal-side communication unit 310 in the image recording unit 350 in association with the angle θ, and it is more preferable that the terminal control unit 320 records the images for inspection received through the terminal-side communication unit 310 in the image recording unit 350 in association with the angle θ and the distance D. Moreover, in the case of the imaging unit 202 including the imaging optical system of which the imaging magnification can be adjusted, it is still more preferable that the images for inspection received through the terminal-side communication unit 310 are recorded in association with the angle θ, the distance D, and the imaging magnification of the imaging optical system.

<Imaging Method>

First Embodiment

Figure 8:
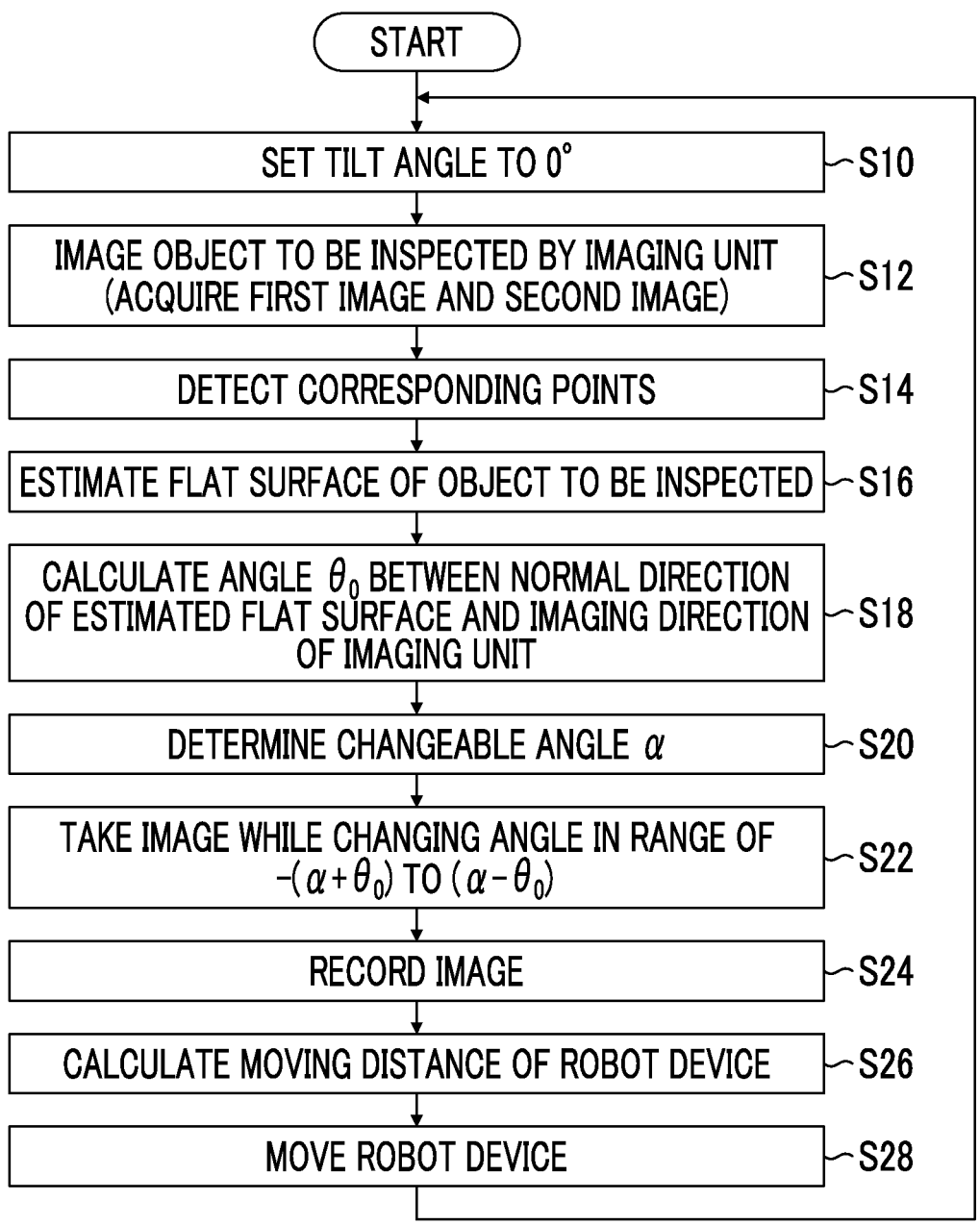
FIG. 8 is a flow chart showing a first embodiment of an imaging method according to the invention.

FIG. 8 is a flow chart showing a first embodiment of an imaging method according to the invention, and FIGS. 9A, 9B, and 9C are schematic diagrams schematically showing the imaging method of the first embodiment.

In FIG. 8, first, the pan/tilt mechanism 120 is manually or automatically controlled so that the tilt angle of the imaging unit 202 is set to 0° (Step S10). In this case, as shown in FIG. 9A, the optical axis direction of the imaging unit 202 is orthogonal to the travel surface for the robot device 100 (the surface of the lower flange of each main girder 2).

Subsequently, the imaging control unit 204 makes the imaging unit 202 image the object to be inspected in a state in which the tilt angle of the imaging unit 202 is 0° (Step S12). Accordingly, the first and second images having parallax (images for angle calculation) are acquired from the imaging unit 202.

The angle calculation unit 220 (FIGS. 5 and 7) detects three or more corresponding points, which are not positioned on the same straight line, on the basis of the first and second images having parallax that are taken by the imaging unit 202 (Step S14), and estimates the flat surface of the object to be inspected on the basis of spatial coordinates of the detected three or more corresponding points on a real space (the flat surface of the object to be inspected) (Step S16). Then, the angle calculation unit 220 calculates an angle θ between the imaging direction of the imaging unit 202 and the normal direction of the estimated flat surface of the object to be inspected (Step S18). The angle θ, which is obtained in a case in which the tilt angle of the imaging unit 202 is 0°, is referred to as an angle $θ_0$.

FIG. 9B shows a case in which the imaging unit 202 is subjected to pan/tilt control so that the angle θ0 is set to 0°. In this case, the imaging unit 202 directly faces the object to be inspected.

Subsequently, the changeable angle α of the imaging unit 202 (that is, the allowable angle range (−α to α)) is determined as shown in FIG. 9C (Step S20). It is preferable that the changeable angle α is determined on the basis of the distance D, the angle of view, or the like.

Next, while an angle with respect to the imaging direction is changed in the range of $-(α+θ_0)$ to $(α-θ_0)$ on the basis of the imaging direction of the imaging unit 202 obtained in a case in which the tilt angle of the imaging unit 202 is 0°, the images for inspection are taken (Step S22). Accordingly, the angle θ between the imaging direction of the imaging unit 202 and the normal direction of the flat surface of the object to be inspected at the time of taking the images for inspection is in the allowable angle range (−α to α).

The images for inspection, which are taken in Step S22, are stored in the image recording unit 350 (Step S24). In this case, it is preferable that the angle θ, the distance D, and the imaging magnification of the imaging optical system are stored in association with the images for inspection to be stored.

Next, the moving distance of the robot device 100 is calculated to image another region of the object to be inspected (a region of the object to be inspected at which the angle θ exceeds the allowable angle range (−α to α)) (Step S26). This moving distance can be calculated on the basis of the angle of view of the imaging unit 202, the changeable angle α, and the distance D.

Subsequently, after the robot device 100 is moved by the moving distance calculated in Step S26 (Step S28), processing returns to Step S10.

Then, the entire region of the object to be inspected can be imaged and images for inspection can be acquired and stored through the repetition of the processing of Step S10 to Step S28.

Second Embodiment

Figure 10:
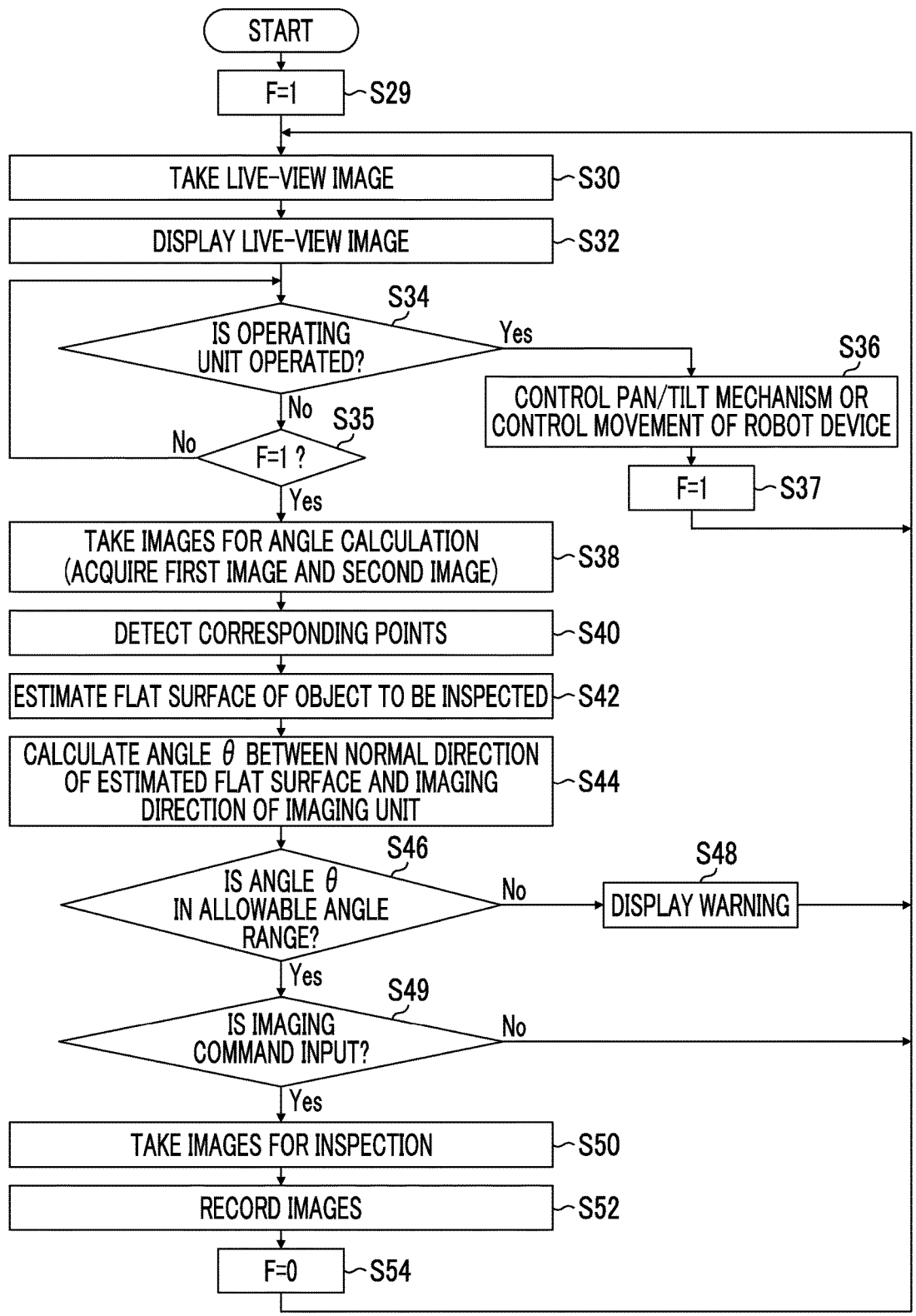
FIG. 10 is a flow chart showing a second embodiment of the imaging method according to the invention.

FIG. 10 is a flow chart showing a second embodiment of the imaging method according to the invention.

In FIG. 10, first, a flag F indicating whether or not the imaging of the current imaging range (the current imaging range specified by the position of the robot device 100 and the pan angle and the tilt angle of the pan/tilt mechanism 120) of an object to be inspected ends is set to 1 (F=1: non-imaging) (Step S29). Subsequently, the imaging control unit 204 makes the imaging unit 202 take a live-view image (Step S30). Accordingly, the live-view image of a video is acquired from the imaging unit 202. In this case, the live-view image may be a first image that is taken by the first imaging part 202A of the imaging unit 202, and may be first and second images (stereoscopic images) having parallax that are taken by the first and second imaging parts 202A and 202B of the imaging unit 202.

The image data of the live-view image, which is taken by the imaging unit 202, are output to the display unit 340 from the imaging unit 202 through the robot-side communication unit 230, the terminal-side communication unit 310, and the terminal control unit 320 and are displayed on the display unit 340 as a live-view image (Step S32).

Next, it is determined whether or not the operating unit 330 (the pan/tilt operating unit and the robot operating unit) of the terminal device 300 is operated (Step S34). If it is determined in Step S34 that the operating unit 330 is operated (in the case of "Yes"), the pan/tilt mechanism 120 is controlled or the movement of the robot device 100 is controlled according to the operation of the operating unit 330 (Step S36). After that, the flag F is set to 1 (non-imaging) (Step S37) and processing proceeds to Step S30.

If it is determined in Step S34 that the operating unit 330 is not operated (in the case of "No"), it is determined whether or not the flag F is set to 1 (Step S35). Since the current imaging range of the object to be inspected has been imaged if the flag F is not 1 (in the case of "No"), processing returns to Step S34. On the other hand, since the current imaging range of the object to be inspected is not imaged if the flag F is 1 (in the case of "Yes"), processing proceeds to Step S38.

In Step S38, the object to be inspected is imaged by the imaging unit 202 (Step S38). Accordingly, the first and second images having parallax (images for angle calculation) are acquired from the imaging unit 202.

Processing of Step S40 to Step S44 is processing for calculating the angle θ, which is formed between the imaging direction of the imaging unit 202 and the normal direction of the estimated flat surface of the object to be inspected, from the acquired images for angle calculation. Since the processing of Step S40 to Step S44 is the same as the processing of Step S14 to Step S18 of the first embodiment of the imaging method shown in FIG. 8, the detailed description thereof will be omitted.

Subsequently, it is determined whether or not the angle θ calculated in Step S44 is in the allowable angle range (−α to α) (Step S46). If it is determined that the angle θ exceeds the allowable angle range (in the case of "No"), the terminal device 300 receiving the determination result thereof displays a warning on the display unit 340 (Step S48) and makes processing proceed to Step S30. Accordingly, an operator is urged to perform the operation (a pan/tilt operation and a robot operation) of the operating unit 330 so that the angle θ is in the allowable angle range. The pan/tilt mechanism 120 may be stopped (the operation of the pan/tilt mechanism 120 in a direction where the angle θ is increased may be stopped) together with the display of a warning in Step S48 or instead of the display of a warning.

On the other hand, if it is determined in Step S46 that the angle θ is the allowable angle range (in the case of "Yes"), it is determined whether or not an imaging command is input (received) from the terminal device 300 (Step S49). If the imaging command is input, the imaging control unit 204 makes the imaging unit 202 take images for inspection (Step S50).

The images for inspection taken in Step S50 are stored in the image recording unit 350 (Step S52). In this case, it is preferable that the angle θ, the distance D, and the imaging magnification of the imaging optical system are stored in association with the images for inspection to be stored.

Subsequently, after the flag F is set to 0 (Step S54), processing returns to Step S30. Since the current imaging range of the object to be inspected has been imaged if the flag F is 0 (F=0), processing of Step S38 or later for the next imaging is not performed until the robot device 100 or the pan/tilt mechanism 120 is driven (that is, until F is set to 1 again in Step S37).

According to the imaging method of the second embodiment, since a warning is displayed in a case in which the angle θ between the imaging direction of the imaging unit 202 and the normal direction of the flat surface of the object to be inspected exceeds the allowable angle range, an operator can operate the pan/tilt operating unit and the like of the operating unit 330 while viewing the live-view image and can operate the pan/tilt operating unit so that the angle θ is in the allowable angle range in a case in which a desired imaging range of the object to be inspected is to be imaged.

Further, in the imaging method of the second embodiment, the pan angle and the tilt angle of the pan/tilt mechanism 120 do not need to be detected and the pan/tilt mechanism 120, which does not depend on the detection accuracy of an angle detector for detecting the pan angle and the tilt angle, can be controlled.

Third Embodiment

Figure 11:
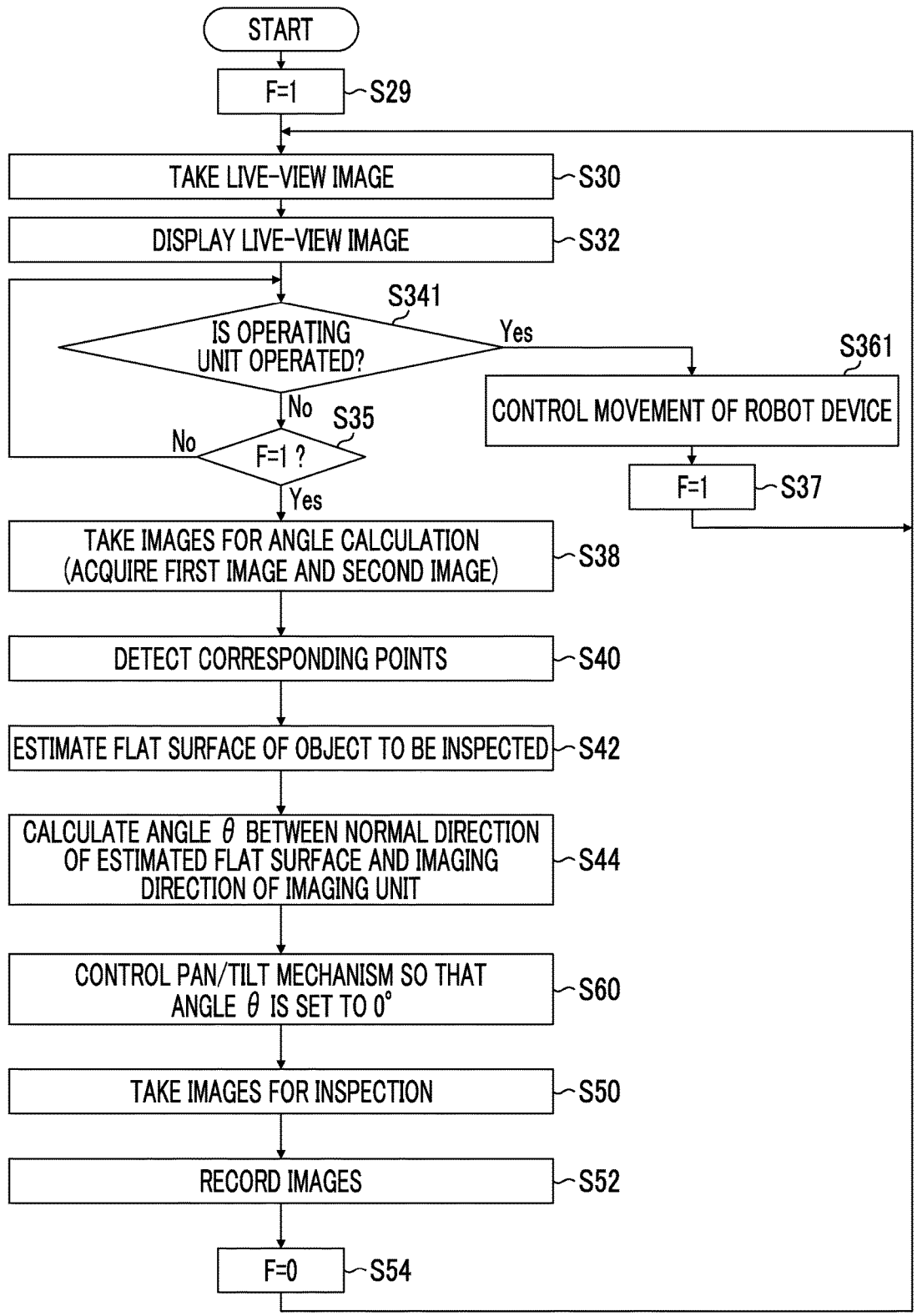
FIG. 11 is a flow chart showing a third embodiment of the imaging method according to the invention.

FIG. 11 is a flow chart showing a third embodiment of the imaging method according to the invention. Steps common to the second embodiment shown in FIG. 10 are denoted by the same reference numerals as the reference numerals of FIG. 10, and the detailed description thereof will be omitted.

The imaging method of the third embodiment shown in FIG. 11 is different from the imaging method of the second embodiment in that the control of the pan/tilt mechanism 120 is automated. Accordingly, in a case in which an operator operates the operating unit 330 of the terminal device 300 while viewing the live-view image, the operator operates only the robot operating unit for moving the robot device 100.

That is, in Step S341, it is determined whether or not the robot operating unit of the operating unit 330 is operated. If it is determined that the robot operating unit is operated, the movement of the robot device 100 is controlled according to the operation of the robot operating unit (Step S361).

The pan/tilt mechanism 120 is automatically controlled in Step S60 so that the angle θ calculated in Step S44 is set to 0° (so that the direction of a normal vector of the estimated flat surface of the object to be inspected corresponds to the imaging direction of the imaging unit 202 (z direction)). Then, in a case in which the angle θ is set to 0° (that is, in a case in which the imaging unit 202 directly faces the object to be inspected), the imaging unit 202 is made to take images for inspection (Step S50). It is preferable that the images for inspection are automatically taken in a case in which the angle θ is set to 0°.

According to the imaging method of the third embodiment, the pan/tilt mechanism 120 is automatically controlled so that the angle θ between the imaging direction of the imaging unit 202 and the normal direction of the flat surface of the object to be inspected is set to 0°. Accordingly, the images for inspection can be taken in a state in which the imaging unit 202 directly faces the object to be inspected and an operator may operate only the robot operating unit of the operating unit 330 while viewing the live-view image in a case in which a desired imaging range of the object to be inspected is to be imaged.

[Others]

In this embodiment, a floor slab of a bridge has been used as an object to be inspected. However, the object to be inspected is not limited thereto, and any object having a flat surface may be used as the object to be inspected.

Further, the terminal device has been provided with the image recording unit for recording images for inspection in this embodiment, but the robot device may be provided with the image recording unit. Furthermore, the invention is not limited to the apparatus in which the robot device and the terminal device are separated from each other, and may also be applied to an apparatus in which the robot device and the terminal device are integrated with each other.

Moreover, it goes without saying that the form and function of the imaging device (movable imaging apparatus) vary depending on an object to be inspected to which the imaging device is applied. For example, various imaging apparatuses, such as movable imaging apparatuses including a bipedal moving body, a quadruped moving body, a moving body travelling by using a caterpillar, and a moving body including an articulated arm (for example, portions, such as an upper arm formed in the shape of a human arm, a forearm, and a hand), are considered as the imaging apparatuses.

The invention is not limited to the above-mentioned embodiments, and may have various modifications without departing from the scope of the invention.

EXPLANATION OF REFERENCES

1: bridge
6: floor slab
10: movable imaging apparatus
100: robot device
108: X-direction drive unit
110: Y-direction drive unit
112: Z-direction drive unit
120: pan/tilt mechanism
130: robot control unit
200: imaging device
202: imaging unit
202A: first imaging part
202B: second imaging part
204: imaging control unit
206: pan/tilt drive unit
210: pan/tilt control unit
220: angle calculation unit
222: corresponding point detection unit
224: spatial coordinate calculation unit
226: flat surface calculation unit
228: determination unit
230: robot-side communication unit
300: terminal device
310: terminal-side communication unit
320: terminal control unit
330: operating unit
340: display unit
350: image recording unit

What is claimed is:

1. An imaging device that images an object to be inspected including a flat surface, the imaging device comprising:
    an imaging unit that includes a plurality of imaging parts taking a plurality of images having parallax;
    a pan/tilt mechanism that rotates the imaging unit in each of a pan direction and a tilt direction;
    an angle calculation unit that calculates an angle between an imaging direction of the imaging unit and a normal direction of the flat surface of the object to be inspected on the basis of the plurality of images taken by the imaging unit and showing the object to be inspected;
    a pan/tilt control unit that controls the pan/tilt mechanism and sets the angle between the imaging direction of the imaging unit and the normal direction of the flat surface of the object to be inspected to an angle within an allowable angle range; and
    an imaging control unit that makes at least one imaging part of the imaging unit take images for inspection showing the object to be inspected to acquire the images for inspection in a case in which the angle between the imaging direction of the imaging unit and the normal direction of the flat surface of the object to be inspected is an angle within the allowable angle range.

2. The imaging device according to claim 1,
    wherein the angle calculation unit includes a corresponding point detection unit that detects three or more corresponding points, which are not positioned on the same straight line, from the plurality of images and a spatial coordinate calculation unit that calculates spatial coordinates of the three or more corresponding points detected by the corresponding point detection unit, and
    the angle calculation unit estimates the flat surface of the object to be inspected from the calculated spatial coordinates of the three or more corresponding points, and calculates the angle between the imaging direction of the imaging unit and the normal direction of the flat surface of the object to be inspected on the basis of the normal direction of the estimated flat surface.

3. The imaging device according to claim 1,
    wherein the allowable angle range is an angle range in which definition of the images for inspection at an end portion of an angle of view most distant from the imaging unit is the minimum definition required for the inspection accuracy of the object to be inspected, in a case in which the angle between the imaging direction of the imaging unit and the normal direction of the flat surface of the object to be inspected is the maximum angle within the allowable angle range.

4. The imaging device according to claim 1,
wherein the imaging unit includes an imaging optical system of which an imaging magnification is adjustable, and
the allowable angle range is set in accordance with the imaging magnification of the imaging optical system.

5. The imaging device according to claim 1, further comprising:
a live-view image display unit that displays a live-view image taken by at least one imaging part of the imaging unit;
a pan/tilt operating unit that outputs pan/tilt commands to the pan/tilt mechanism by a manual operation; and
a determination unit that determines whether or not the angle calculated by the angle calculation unit exceeds the allowable angle range,
wherein the pan/tilt control unit controls the pan/tilt mechanism on the basis of the pan/tilt commands output from the pan/tilt operating unit, and stops the pan/tilt mechanism in a case in which the determination unit determines that the angle calculated by the angle calculation unit exceeds the allowable angle range.

6. The imaging device according to claim 1, further comprising:
a live-view image display unit that displays a live-view image taken by at least one imaging part of the imaging unit;
a pan/tilt operating unit that outputs pan/tilt commands to the pan/tilt mechanism by a manual operation;
a determination unit that determines whether or not the angle calculated by the angle calculation unit exceeds the allowable angle range; and
an information unit that issues a warning in a case in which the determination unit determines that the angle calculated by the angle calculation unit exceeds the allowable angle range,
wherein the pan/tilt control unit controls the pan/tilt mechanism on the basis of the pan/tilt commands output from the pan/tilt operating unit.

7. The imaging device according to claim 1,
wherein the pan/tilt control unit automatically controls the pan/tilt mechanism on the basis of the angle calculated by the angle calculation unit to set the angle between the imaging direction of the imaging unit and the normal direction of the flat surface of the object to be inspected to 0°.

8. The imaging device according to claim 1, further comprising:
a moving body on which the imaging device is mounted and which moves the imaging device along the flat surface of the object to be inspected;
a moving body operating unit that outputs a movement command to the moving body by a manual operation; and
a moving body control unit that moves the moving body on the basis of the movement command output from the moving body operating unit.

9. The imaging device according to claim 1, further comprising:
an image recording unit that records the images for inspection acquired by the imaging control unit in association with the angle between the imaging direction of the imaging unit and the normal direction of the flat surface of the object to be inspected at the time of taking the images for inspection.

10. The imaging device according to claim 1, further comprising:
a distance calculation unit that calculates a distance between the object to be inspected and the imaging unit in the imaging direction of the imaging unit on the basis of the plurality of images taken by the imaging unit and showing the object to be inspected; and
an image recording unit that records the images for inspection acquired by the imaging control unit in association with the angle between the imaging direction of the imaging unit and the normal direction of the flat surface of the object to be inspected at the time of taking the images for inspection and the distance calculated by the distance calculation unit.

11. The imaging device according to claim 10,
wherein the imaging unit includes an imaging optical system of which an imaging magnification is adjustable, and
the image recording unit records the images for inspection in association with the angle between the imaging direction of the imaging unit and the normal direction of the flat surface of the object to be inspected at the time of taking the images for inspection, the distance calculated by the distance calculation unit, and the imaging magnification of the imaging optical system.

12. The imaging device according to claim 9,
wherein the angle calculation unit calculates the angle between the imaging direction of the imaging unit and the normal direction of the flat surface of the object to be inspected on the basis of the plurality of images that are taken and acquired by the imaging unit at the time of taking the images for inspection and show the object to be inspected.

13. An imaging method of imaging an object to be inspected including a flat surface, the imaging method comprising:
a step of taking a plurality of images having parallax by an imaging unit including a plurality of imaging parts;
a step of calculating an angle between an imaging direction of the imaging unit and a normal direction of the flat surface of the object to be inspected on the basis of the plurality of images, which are taken by the imaging unit and show the object to be inspected, by an angle calculation unit;
a step of controlling a pan/tilt mechanism, which rotates the imaging unit in each of a pan direction and a tilt direction, and setting the angle between the imaging direction of the imaging unit and the normal direction of the flat surface of the object to be inspected to an angle within an allowable angle range; and
a step of making at least one imaging part of the imaging unit take images for inspection showing the object to be inspected to acquire the images for inspection in a case in which the angle between the imaging direction of the imaging unit and the normal direction of the flat surface of the object to be inspected is an angle within the allowable angle range.

14. The imaging method according to claim 13,
wherein the step of calculating the angle includes a step of detecting three or more corresponding points, which are not positioned on the same straight line, from the plurality of images, and a step of calculating spatial coordinates of the detected three or more corresponding points, and the flat surface of the object to be inspected is estimated from the calculated spatial coordinates of the three or more corresponding points, and the angle between the imaging direction of the imaging unit and the normal direction of the flat surface of the object to be inspected is calculated on the basis of the normal direction of the estimated flat surface.

15. The imaging method according to claim 13, wherein the allowable angle range is an angle range in which definition of the images for inspection at an end portion of an angle of view most distant from the imaging unit is the minimum definition required for the inspection accuracy of the object to be inspected, in a case in which the angle between the imaging direction of the imaging unit and the normal direction of the flat surface of the object to be inspected is the maximum angle within the allowable angle range.

* * * * *